United States Patent [19]

Schlecker et al.

[11] Patent Number: 5,039,701

[45] Date of Patent: Aug. 13, 1991

[54] NOVEL BENZOFURAN DERIVATIVES AND THERAPEUTIC AGENTS CONTAINING THEM

[75] Inventors: Rainer Schlecker, Bissersheim; Manfred Raschack, Weisenheim; Josef Gries, Wachenheim, all of Fed. Rep. of Germany

[73] Assignee: BASF Aktiengesellschaft, Ludwigshafen, Fed. Rep. of Germany

[21] Appl. No.: 233,745

[22] Filed: Aug. 19, 1988

[30] Foreign Application Priority Data

Aug. 20, 1987 [DE] Fed. Rep. of Germany ....... 3727736

[51] Int. Cl.$^5$ ..................... A61K 31/34; C07D 307/78
[52] U.S. Cl. ..................... 514/469; 514/253; 514/320; 514/422; 544/376; 546/196; 548/525; 549/467
[58] Field of Search ........................ 544/376; 546/196; 548/525; 549/467; 514/253, 320, 422, 469

[56] References Cited

U.S. PATENT DOCUMENTS 3,850,937 11/1974 Fauran et al. ..................... 546/196
3,862,176 1/1975 Fauran et al. ..................... 549/467

FOREIGN PATENT DOCUMENTS 2235941 2/1973 Fed. Rep. of Germany .
2238115 5/1973 Fed. Rep. of Germany .

OTHER PUBLICATIONS

Gimet et al., "Chemical Abstracts", vol. 87, 1977, col. 87:58451k.
Rigal et al., "Chemical Abstracts", vol. 87; 1977, col. 87:73300d.
Hawkins et al., "Chemical Abstracts", vol. 94, 1981, col. 94:149958s.
Schlecker et al., "Chemical Abstracts", vol. 111, 1989, col. 111:57530n.

Primary Examiner—C. Warren Ivy
Assistant Examiner—Celia Chang
Attorney, Agent, or Firm—Oblon, Spivak, McClelland, Maier & Neustadt, P.C.

[57] ABSTRACT

Benzofuran derivatives of the formula I

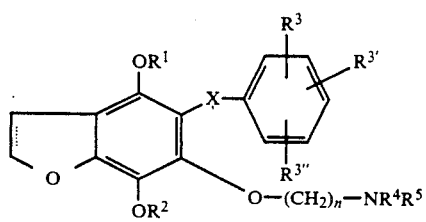

where $R^1$ to $R^5$ and X have the meanings stated in the description, and therapeutic agents containing these derivatives.

4 Claims, No Drawings

NOVEL BENZOFURAN DERIVATIVES AND THERAPEUTIC AGENTS CONTAINING THEM

The present invention relates to novel benzofuran derivatives of the formula I and therapeutic agents which contain these derivatives and are used for the treatment of cardiovascular disorders, coronary heart diseases, vasospasms and hypertension.

German Laid-Open Applications DOS 2,235,941 and DOS 2,238,115 describe benzofuran derivatives which have a powerful in vitro calcium-antagonistic activity but have only weak enteral activity.

We have found, surprisingly, that the benzofuran derivatives of the formula

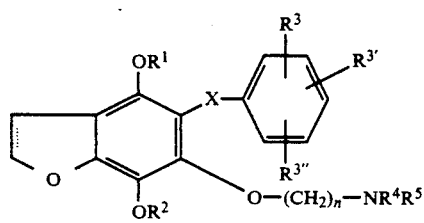

where $R^1$ and $R^2$ independently of one another are each hydrogen, alkyl or phenylalkyl where alkyl in each case is of 1 to 4 carbon atoms, $R^3$, $R^{3'}$ and $R^{3''}$ are each hydrogen, benzyloxy, fluorine, chlorine, bromine, hydroxyl or $C_{1-6}$-alkoxy, or are each amine which is monosubstituted or disubstituted by $C_1$-$C_4$-alkyl or $C_1$-$C_4$-acyl, or are each nitro, hydroxymethyl or $C_1$-$C_4$-alkyl, and two adjacent radicals $R^3$ and $R^{3'}$ together may form the radical —CH=CH—NH—, $R^4$ and $R^5$ independently of one another are each hydrogen, $C_1$-$C_4$-alkyl or phenylalkyl where alkyl is of 1 to 4 carbon atoms and the phenyl nucleus may be monosubstituted or disubstituted by fluorine, chlorine, bromine, $C_1$-$C_4$-alkoxy, unsubstituted or mono-or di-$C_1$-$C_4$-alkyl-substituted amine or nitro, or $R^4$ and $R^5$ together form a 3-membered to 6-membered chain which may contain an oxygen or nitrogen atom and may be bonded to a benzene ring which in turn may be substituted by fluorine, chlorine, bromine, $C_1$-$C_4$-alkoxy, unsubstituted or mono- or di-$C_1$-$C_4$-alkyl-substituted amine or nitro, X is —CO—CH=CH—, —CO—CH$_2$—CH$_2$— or —CHOH—CH$_2$—CH$_2$—, n is 2 or 3 and

|:

is a single or double bond, with the proviso that if $R^1$ and $R^2$ are simultaneously methyl, $R^4$ can only be hydrogen or alkyl and $R^5$ can only be unsubstituted or substituted phenylalkyl or $R^4$ and $R^5$ together form a 3-membered to 6-membered chain which may contain an oxygen or nitrogen atom and is bonded to an unsubstituted or substituted benzene ring, have substantially higher oral availability while retaining the calcium-antagonistic activity.

The novel compounds of the formula I can in principle be prepared by the processes as described in German Patent Application P 37 10 469.1.

The compounds of the general formula I where X is —CO—CH$_2$CH$_2$ can be prepared from the compounds of the formula I in which X is —CO—CH=CH— by catalytic hydrogenation of the double bond by methods known from the literature, as described in, for example, R. N. Rylander, Catalytic Hydrogenation over Pt Metals, Acad. Press, New York, page 282, 1967. Particularly suitable catalysts are metal catalysts, such as palladium on carbon or Raney nickel in alcohol.

The compounds of the general formula I in which X is —CH(OH)—CH$_2$CH$_2$ can be prepared by reduction of the compounds of the general formula I where X is —CO—CH$_2$CH$_2$, with a metal hydride by a conventional method, as described in Houben-Weyl, Methoden der org. Chemie, 4th edition, G. Thieme Verlag Stuttgart 1984, volume 6/1b, page 145. Examples of suitable metal hydrides are LiAlH$_4$ in ethers and NaBH$_4$ in alcohols, such as ethanol or isopropanol.

These compounds can also be prepared from the compounds of the formula I where X is —CO—CH=CH— by catalytic hydrogenation as described in Houben-Weyl, vol. 6/1b, page 61, or by reduction with a metal hydride, as described in Houben-Weyl, 4th edition, (1981), vol. 4/1d, page 297 and in German Laid-Open Application DOS 2,235,941.

The compounds of the formula I where X is —CO—CH=CH— are synthesized from the acetophenones of the formula III by condensation with aromatic aldehydes by known methods, as described in, for example, Org. Reactions vol. 16, page 1 et seq., John Wiley Publishers, New York 1968. Examples of suitable condensing agents are alkali metal hydroxides in aqueous alcoholic solution.

The compounds of the formula III where $R^1$ and $R^2$ are each CH$_3$ can be obtained by alkylation of the o-hydroxyacetophenone khellinone II (J. Amer. Chem. Soc. 72 (1950), 1613) with a haloalkylamine, as described in Chimie Therapeutique 4 (1973), 475 and German Patent Application P 37 10 469.1. The alkylation of II

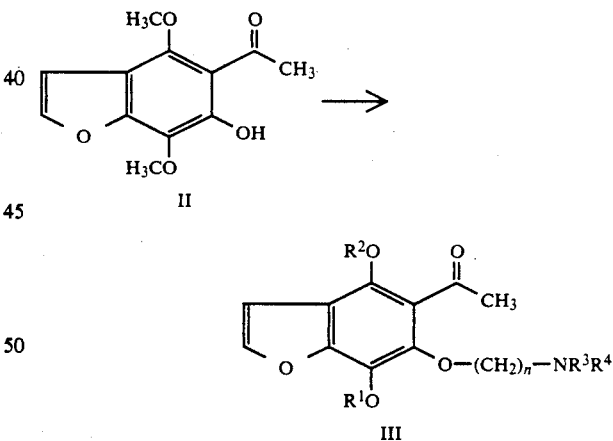

can also be carried out with aminoalcohols under conditions of the Mitsunobu method (Synth. 1981, 1).

The compounds of the formula III where $R^1$ and $R^2$ is not CH$_3$ can be prepared by alkylation of the hydroxyacetophenones IV

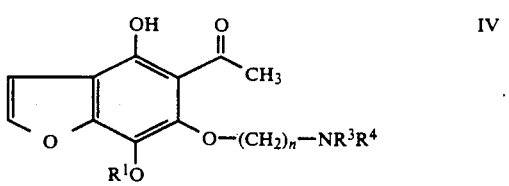

by a conventional method of phenol synthesis (Houben-Weyl vol. VI/3, page 49 et seq.). For example, the alkylation can be carried out with an alkyl halide using an alkali metal carbonate as the base in acetone as a solvent, or using a metal hydride in an aprotic solvent, such as dimethylformamide or tetrahydrofuran.

The compounds IV are obtainable via hydrogenolysis of the benzyl ether V by a known method (Houben-Weyl vol. 4/1c, page 385 et seq.). The debenzylation is preferably carried out at room temperature in order to avoid hydrogenation of the furan ring.

The compounds V are synthesized from the hydroxyacetophenones VI by the process described for the preparation of III (where $R^1$ and $R^2$ are each $CH_3$).

The hydroxyacetophenone VI is prepared by alkaline ring cleavage of the pyrone VII by the method described in German Patent Application P 37 10 469.1.

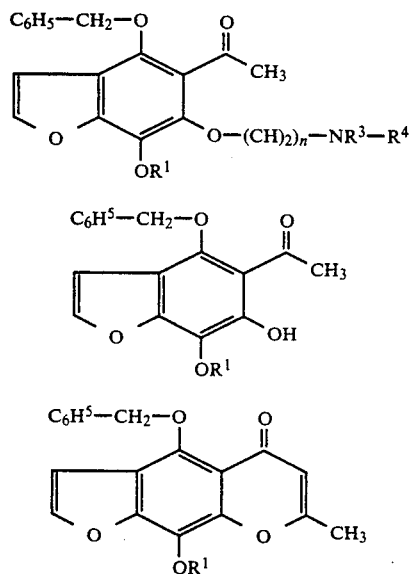

The compounds of the general formula I in which the furan ring is hydrogenated are synthesized in a similar manner, a suitable intermediate, for example II, being converted into the corresponding dihydrobenzofuran derivative by a conventional method of catalytic hydrogenation.

The hydrogenation is preferably carried out at slightly elevated temperatures of from 20° to 100° C. using Pd or Pt as catalyst.

The novel compounds of the formula I in which X is $CHOH-CH_2CH_2$ possess a center of chirality and are obtained as racemates, which can be resolved into the optically active antipodes by a known method, for example by formation of diastereomeric salts with optically active acids or dibenzoyltartaric acid, camphor-10-sulfonic acid or ditolytartaric acid.

If necessary, the resulting novel compounds can be converted into addition salts with a physiologically tolerated acid. A list of conventional physiologically tolerated acids is given in Fortschritte der Arzbneimittelforschung 1966, Birkhäuser Verlag, vol. 10, pages 224–285, Germany, Switzerland.

The addition salts with acid are, as a rule, obtained in a conventional manner by mixing the free base or a solution thereof with the corresponding acid or a solution thereof in an organic solvent, for example a lower alcohol, such as methanol, ethanol or propanol, or a lower ketone, such as acetone, methyl ethyl ketone or methyl isobutyl ketone, or an ether, such as diethyl ether, tetrahydrofuran or dioxane. To improve deposition of crystals, mixtures of the stated solvents may be used. Moreover, pharmaceutically acceptable aqueous solutions of acid addition compounds of the aminopropanol derivatives of the formula I can be prepared by dissolving the free bases in an aqueous acid solution.

The novel compounds (of the general formula I) and their physiologically tolerated addition salts with acids have useful pharmacological properties. They are highly active Ca antagonists and consequently produce in vitro relaxation of the blood vessels. They also reduce the arterial blood pressure in normotonic and hypertensive experimental animals. They are furthermore capable of protecting the myocardium from the loss of high-energy phosphates (e.g. adenosine triphosphate, ATP) which occurs during anoxic respiration, i.e. they have a cardioprotective action.

Because of the pronounced Ca-antagonistic action and the superior antihypertensive and cardioprotective action, the novel compounds are suitable for the enteral treatment of cardiovascular disorders, in particular coronary heart disease, and of vasospasms and hypertension.

The dose depends on the age, condition and weight of the patient and on the route of administration. As a rule, the daily dose of active compound is about 10–1000 mg per patient.

The novel compounds can be used in the conventional solid pharmaceutical enteral administration forms, for example as tablets, film tablets, capsules, powders, granules, coated tablets or suppositories. These are prepared in a conventional manner and to do so the active compounds can be mixed with the conventional pharmaceutical auxiliaries, such as tablet binders, fillers, preservatives, tablet disintegrators, flow regulators, plasticizers, wetting agents, dispersants, emulsifiers, solvents, retarding agents and antioxidants (cf. H. Sucker et al.: Pharmazeutische Technologie, Thieme-Verlag, Stüttgart, 1978). The administration forms thus obtained normally contain the active compound in an amount of from 1 to 99% by weight.

The following method is used to demonstrate the pharmacological activity:

Antihypertensive action

The substances are administered orally to spontaneously hypertensive male Okamoto rats (SHR) weighing 270–380 g (5–10 animals per dose). The systolic blood pressure is determined prior to administration and 2 hours afterwards non-invasively at the tail of the rat with the aid of piezoelectric crystal transducers by a plethysmographic method. The dose which reduces the systolic blood pressure by 20% is determined as the ED 20%, the values for untreated control animals being taken into account.

TABLE

Blood pressure lowering doses (ED 20%, mg/kg) in conscious spontaneously hypertensive rats (SHR)

| Example | Antihypertensive activity SHR p.o. | |
|---|---|---|
| | ED 20% | R.P.* |
| 1 | 5.0 | 17.2 |
| 2 | 6.7 | 12.7 |
| 3 | 21.5 | 4.0 |
| 5 | 21.5 | 4.0 |
| 7 | 5.5 | 15.6 |

TABLE-continued

Blood pressure lowering doses (ED 20%, mg/kg) in conscious spontaneously hypertensive rats (SHR)

| Example | Antihypertensive activity SHR p.o. | |
|---|---|---|
| | ED 20% | R.P.* |
| 9 | 21.5 | 4.0 |
| 18 | 13.1 | 6.5 |
| 20 | 8.0 | 10.7 |
| 21 | 12.6 | 6.8 |
| 23 | 21.5 | 4.0 |
| 25 | 25.7 | 3.3 |
| 27 | 16.7 | 5.1 |
| Piprofurol | 85.5 | 1 |

*Relative potency; Piprofurol = 1.0

The results show that the orally administered novel substances have good hypotensive and antihypertensive actions.

EXAMPLES FOR THE PREPARATION OF THE STARTING COMPOUNDS

5-Acetyl-4,7-dimethoxy-6-[3-((2-(3,4-dimethoxyphenyl)-ethyl)-methylamino)propoxy]-benzofuran 39 g of 5-acetyl-6-hydroxy-4,7-dimethoxybenzofuran are refluxed with 40 g of 3-chloropropyl-(2-(3,4-dimethoxyphenyl)-ethyl)-methylamine in 250 ml of methyl ethyl ketone for 14 hours. The mixture is filtered, the solvent is stripped off and the oily residue is dissolved in dilute HCl. The aqueous phase is washed with ether, rendered alkaline with dilute sodium hydroxide solution and extracted with ether. Stripping off the solvent gives 45 g of crude oily product which is further reacted without purification.

4-Benzyloxy-9-methoxy-7-methylfuro[3,2-g]chromone 95 g of 4-hydroxy-9-methoxy-7-methfuro[3,2-g]chromone in 1000 ml of methyl ethyl ketone are refluxed with 100 g of benzyl bromide and 210 g of $K_2CO_3$ for 15 hours. 1000 ml of $CH_2Cl_2$ are added to the mixture, which is then filtered, and the solvent is distilled off. After treatment with petroleum ether, the residue gives 123 g of VII (where $R^1$ is $CH_3$) as a yellowish oil.

5-Acetyl-4-benzyloxy-6-hydroxy-7-methoxybenzofuran 113 g of VII (where $R^1$ is $CH_3$) are added a little at a time to a solution of 67 g of KOH in 1000 ml of water at 75° C. The mixture is refluxed for 3 hours and then cooled and filtered. The filtrate is acidified with 110 ml of concentrated hydrochloric acid, and the precipitated residue is filtered off under suction and dried to give 115 g of V (where $R^1$ is $CH_3$).

5-Acetyl-4-benzyloxy-7-methoxy-6-(2-N-piperidinoethoxy)-benzofuran 50 g of VI (where $R^1$ is $CH_3$) in 400 ml of methyl ethyl ketone are refluxed with 35 g of chloroethylpiperidine and 90 g of $K_2CO_3$ for 5 hours. The mixture is filtered and the filtrate is evaporated down. The residue is partitioned between water and ether. 69 g of V (where $R^1$ is $CH_3$) are obtained as a yellowish oil.

5-Acetyl-4-hydroxy-7-methoxy-6-(2-N-piperidinoethoxy)-benzofuran 18.5 g of V (where $R^1$ is $CH_3$ and $R^3$ and $R^4$ together are pentamethylene) are dissolved in 150 ml of ethyl acetate and the solution is stirred with 1 g of Pd/C under atmospheric pressure at room temperature in a hydrogenation apparatus until the absorption of hydrogen has ended. The catalyst is filtered off and the filtrate is evaporated down. The residue gives 16 g of the desired product.

5-Acetyl-4-ethoxy-7-methoxy-(2-piperidinoethoxy)-benzofuran 3.3 g 5-Acetyl-4-hydroxy-7-methoxy-6-(2-piperidinoethoxy)-benzofuran in 2 ml of dimethylformamide are added dropwise to a suspension of 0.4 g of NaH (55% strength in liquid paraffin) in 10 ml of dimethylformamide at room temperature. The mixture is stirred for 30 minutes, after which 2.1 g of ethyl iodide are added. Stirring is continued overnight and the mixture is poured onto ice and extracted with ether. The ether phase is washed with water and evaporated down. The residue is partitioned between $CH_2Cl_2$ and 1N HCl. The organic phase is dried and evaporated down to give 2.0 g of the hydrochloride and evaporated down to give 2.0 g of the hydrochloride of the desired compound.

The following are prepared in a similar manner:

5-acetyl-4-ethoxy-7-methoxy-6-[3-((2-(3,4-dimethoxyphenyl)-ethyl)-methylamino)-propoxy]-benzofuran, oil 5-acetyl-4,7-dimethoxy-6-[3-((2-(3-methoxyphenyl)-ethylmethylamino)-propoxy]-benzofuran, oil 5-acetyl-4-ethoxy-7-methoxy-6-[3-((2-(3-methoxyphenyl)-ethyl)-methylamino)-propoxy]-benzofuran, oil 5-acetyl-4,7-dimethoxy-6-[3-(4-(2-methoxyphenyl)-piperazinyl)-propoxy]-benzofuran, oil 5-acetyl-4,7-dimethoxy-6-[3-(4-phenylpiperidinyl)-propoxy]-benzofuran, oil 5-acetyl-2,3-dihydro-6-hydroxy-4,7-dimethoxybenzofuran 10 g of 5-acetyl-6-hydroxy-4,7-dimethoxybenzofuran in 100 ml of methanol are hydrogenated using 2 g of Pd/C (10%) at room temperature and under slightly superatmospheric pressure. When the absorption of hydrogen is complete, the mixture is filtered and the solvent is distilled off. 9.7 g of the desired product of melting point 100°-101° C. are obtained.

Examples of the preparation of the novel compounds:

EXAMPLE 1

1-[4,7-Dimethoxy-6-[3-((2-(3,4-dimethoxyphenyl)-ethyl)-methylamino)-propoxy]-benzofuran-5-yl]-3-(4-hydroxyphenyl)-propenone 8 g of acetyl-4,7-dimethoxy-6-[3-((2-(3,4-dimethoxyphenyl)-ethyl)-methylamino)-propoxy]-benzofuran and 4 g of 4-hydroxybenzaldehyde in 60 ml of ethanol and 20 g of concentrated sodium hydroxide solution were stirred overnight at room temperature. The mixture was poured onto ice, neutralized with dilute hydrochloric acid and extracted with $CH_2Cl_2$. The organic phase was washed again with water, dried and evaporated down. The residue was dissolved in $CH_2Cl_2$ using an equimolar amount of oxalic acid. The product was precipitated as the oxalate by adding ether.

Yield: 2.8 g, m.p. 60° C.

Examples 2 to 20 in Table 1 were synthesized in a similar manner. The structure of all compounds were ascertained by NMR spectroscopy.

EXAMPLE 21

1-[4-Ethoxy-7-methoxy-6-[3-((2-(3,4-dimethoxyphenyl)-ethyl)-methylamino)-propoxy)-benzofuran-5-yl]-3-(4-hydroxyphenyl)-propanone 15 of the chalkone from Example 2 in 200 ml of methanol were hydrogenated at room temperature using 1.5 g of Pd/C until the calculated amount of hydrogen had been absorbed. The solvent was distilled off and the residue was purified by chromatography. 2.1 g of oily product were obtained.

Examples 22 to 24 in Table 2 were synthesized in a similar manner.

EXAMPLE 25

1-(4-Ethoxy-7-methoxy-6-(2-N-piperidinoethoxy)benzofuran-5-yl)-3-(4-hydroxyphenyl)-propan-1-ol 3.7 g of $NaBH_4$ were added to 9 g of 1-(4-ethoxy-7-methoxy-6-(2-N-piperidinoethoxy)-benzofuran-5-yl)-3-(4-hydroxyphenyl)-propenone in 40 ml of ethanol and 7 g of pyridine at room temperature, and the mixture was refluxed for 5 hours. It was then poured onto iced water, neutralized with dilute HCl and extracted with $CH_2Cl_2$. The organic phase was dried, the solvent was distilled off and the residue was chromatographed over silica gel (8:1 $CH_2Cl_2/CH_3OH$).

3.7 g of product of melting point 132° C. were obtained.

The compounds in Table 3 were prepared in a similar manner.

TABLE 1

| Example | $R^1$ | $R^2$ | n | $NR^4R^5$ | $R^3$ | $R^{3'}$ | $R^{3''}$ | Mp. [°C.] |
|---|---|---|---|---|---|---|---|---|
| 2 | $C_2H_3$ | $CH_3$ | 3 | $N(CH_3)$–CH$_2$CH$_2$–(3-OCH$_3$-phenyl) | 4-OH | H | H | oil |
| 3 | $CH_3$ | $CH_3$ | 3 | $N(CH_3)$–CH$_2$CH$_2$–(3-OCH$_3$-phenyl) | 4-OH | H | H | oil |
| 4 | $CH_3$ | $CH_3$ | 3 | $N(CH_3)$–CH$_2$CH$_2$–(3,4-di-OCH$_3$-phenyl) | 4-F | H | H | oil |
| 5 | $CH_3$ | $CH_3$ | 3 | $N(CH_3)$–CH$_2$CH$_2$–(3,4-di-OCH$_3$-phenyl) | H | H | H | oil |
| 6 | $CH_3$ | $CH_3$ | 3 | piperazinyl-(2-OCH$_3$-phenyl) | 4-OH | H | H | 67 |
| 7 | $C_2H_5$ | $CH_3$ | 3 | $N(CH_3)$–CH$_2$CH$_2$–(3-OCH$_3$-phenyl) | 4-OH | H | H | oil |
| 8 | $CH_3$ | $CH_3$ | 3 | $N(CH_3)$–CH$_2$CH$_2$–(3,4-di-OCH$_3$-phenyl) | 4-OCH$_3$ | 4-OC$_2$H$_5$ | H | oil |

TABLE 1-continued

[Structure: benzofuran with OR¹ (top), OR² (bottom), O-(CH₂)ₙ-NR⁴R⁵ substituent, and C(O)-CH=CH- linker to a phenyl ring bearing R³, R³', R³'']

| Example | R¹ | R² | n | NR⁴R⁵ | R³ | R³' | R³'' | Mp. [°C] |
|---|---|---|---|---|---|---|---|---|
| 9 | CH₃ | CH₃ | 3 | N(CH₃)-CH₂CH₂-(3,4-dimethoxyphenyl) | H | 4-OCH₂-C₆H₅ | H | oil |
| 10 | C₃H₇ | CH₃ | 3 | N(CH₃)-CH₂CH₂-(3,4-dimethoxyphenyl) | 4-OH | H | H | oil |
| 11 | CH₃ | CH₃ | 3 | N(CH₃)-CH₂CH₂-(3,4-dimethoxyphenyl) | 4-OH, | 3-OCH₃ | H | oil |
| 12 | CH₃ | CH₃ | 3 | N(CH₃)-CH₂CH₂-(3,4-dimethoxyphenyl) | 3-OH | H | H | oil |
| 13 | CH₃ | CH₃ | 3 | N(CH₃)-CH₂CH₂-(3,4-dimethoxyphenyl) | 4-NHCOCH₃ | H | H | oil |
| 14 | CH₃ | CH₃ | 3 | 4-phenylpiperidin-1-yl | 4-OH | H | H | 158 |
| 15 | CH₃ | CH₃ | 3 | 4-benzylpiperidin-1-yl | 4-OH | H | H | 170 |
| 16 | CH₃ | CH₃ | 3 | 4-(4-fluorophenyl)piperazin-1-yl | 4-OH | H | H | 160 |
| 17 | CH₃ | CH₃ | 3 | N(CH₃)-CH₂CH₂-(3,4-dimethoxyphenyl) | 3-Cl | 5-Cl | 4-OH | 185 |
| 18 | CH₃ | CH₃ | 3 | N(CH₃)-CH₂CH₂-(3,4-dimethoxyphenyl) | 4-NH—CH=CH-3 (fused pyrrole) | H | H | 70 |
| 19 | CH₃ | CH₃ | 3 | N(CH₃)-CH₂CH₂-(3,4-dimethoxyphenyl) | 4-OH, 3-CH₂OH | H | H | 89 |

TABLE 1-continued

Structure: benzofuran with OR¹ (top), OR² (bottom), C(O)—CH=CH—phenyl(R³, R³', R³'') substituent, and O—(CH₂)ₙ—NR⁴R⁵ substituent.

| Example | R¹ | R² | n | NR⁴R⁵ | R³ | R³' | R³'' | Mp. [°C] |
|---|---|---|---|---|---|---|---|---|
| 20 | | | | | | | | oil |

Example 20: 2,3-dihydrobenzofuran with OCH₃ (top), OCH₃ (bottom), C(O)—CH=CH—C₆H₄—OH (4-OH), and O—(CH₂)₃—N(CH₃)—(CH₂)₂—(3,4-dimethoxyphenyl).

TABLE 2

Structure: benzofuran with OR¹, OR², C(O)—CH₂—CH₂—phenyl(R³, R³', R³''), and O—(CH₂)ₙ—NR⁴R⁵.

| Example | R¹ | R² | n | NR⁴R⁵ | R³ | Mp. [°C] |
|---|---|---|---|---|---|---|
| 22 | CH₃ | CH₃ | 3 | —N(CH₃)—(CH₂)₂—(3-methoxyphenyl) | 4-OH | oil |
| 23 | C₂H₅ | CH₃ | 3 | —N(CH₃)—(CH₂)₂—(3-methoxyphenyl) | 4-OH | oil |
| 24 | CH₃ | CH₃ | 3 | —N(CH₃)—(CH₂)₂—(3,4-dimethoxyphenyl) | H | oil |

TABLE 3

Structure: benzofuran with OR¹, OR², CHOH—CH₂—CH₂—phenyl(R³, R³', R³''), and O—(CH₂)ₙ—NR⁴R⁵.

| Example | R¹ | R² | n | NR⁴R⁵ | R³ | Mp. [°C] |
|---|---|---|---|---|---|---|
| 25 | C₂H₅ | CH₃ | 2 | piperidino | 4-OH | 132 |

TABLE 3-continued

Structure:
$$\text{benzofuran with } OR^1, OR^2, \text{CHOH—CH}_2\text{—CH}_2\text{—phenyl}(R^3, R^{3'}, R^{3''}), O\text{—(CH}_2)_n\text{—NR}^4R^5$$

| Example | $R^1$ | $R^2$ | n | $NR^4R^5$ | $R^3$ | Mp. [°C.] |
|---|---|---|---|---|---|---|
| 26 | $C_6H_5CH_2$ | $CH_3$ | 2 | piperidine | 4-OH | 140 |
| 27 | $CH_3$ | $CH_3$ | 3 | $N(CH_3)$-CH$_2$CH$_2$-(3,4-dimethoxyphenyl) | H | oil |
| 28 | $C_2H_5$ | $CH_3$ | 2 | pyrrolidine | 4-N(CH$_3$)$_2$ | 139 (fumarate) |
| 29 | $C_3H_7$ | $CH_3$ | 2 | pyrrolidine | 4-OH | 122 |
| 30 | $CH_3$ | $CH_3$ | 3 | $N(CH_3)$-CH$_2$CH$_2$-(3,4-dimethoxyphenyl) | 4-OH | oil |
| 31 | $CH_3$ | $CH_3$ | 3 | $N(CH_3)$-CH$_2$CH$_2$-(3,4-dimethoxyphenyl) | H | oil |
| 32 | $CH_3$ | $CH_3$ | 3 | piperazine-(2-methoxyphenyl) | 4-OH | oil |
| 33 | $CH_3$ | $CH_3$ | 3 | $N(CH_3)$-CH$_2$CH$_2$-(3,4-dimethoxyphenyl) | 4-F | oil |

We claim:

1. A benzofuran compound of the formula

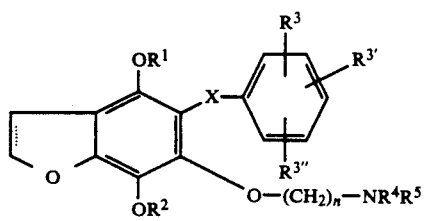

I wherein $R^1$ and $R^2$ independently of one another are each alkyl or phenylalkyl where alkyl in each case is of 1 to 4 carbon atoms, $R^3$, $R^{3'}$ and $R^{3''}$ are each hydrogen, benzyloxy, fluorine, chlorine, bromine, hydroxyl or $C_{1-6}$-alkoxy, or are each amine which is monosubstituted or disubstituted by $C_1$-$C_4$-alkyl or $C_1$-$C_4$-acyl, or are each nitro, hydroxymethyl or $C_1$-$C_4$-alkyl, and two adjacent radicals $R^3$ and $R^{3'}$ together may form the radical —CH=CH—NH—, $R^4$ is $C_1$-$C_4$-alkyl and $R^5$ is phenylalkyl where alkyl is of 1 to 4 carbon atoms and the phenyl nucleus is unsubstituted or monosubstituted or disubstituted by $C_1$-$C_4$-alkoxy, X is —CO—CH=CH—, —CO—CH$_2$—CH$_2$— or —CHOH—CH$_2$—CH$_2$—, n is 2 or 3 and is a single or double bond.

2. A therapeutic pharmaceutical composition for enteral use for the treatment of coronary heart disease, vasospasms and hypertension, which, in addition to a pharmaceutically acceptable carrier, contains an effective calcium-antagonistic amount of a benzofuran compound of the formula I as claimed in claim 1.

3. A therapeutic pharmaceutical composition for enteral use which contains, in addition to a pharmaceutically acceptable carrier, from 10 to 1000 mg of a benzofuran compound of the formula I as claimed in claim 1 per individual dose.

4. A method of treating coronary heart disease, vasospasms and hypertension in a subject in need thereof, which comprises administering to the subject an effective calcium-antagonistic amount of a benzofuran compound of the formula I as claimed in claim 1.

* * * * *